United States Patent
Yuan et al.

(10) Patent No.: US 9,597,142 B2
(45) Date of Patent: Mar. 21, 2017

(54) METHOD AND SYSTEM RELATED TO ELECTROSURGICAL PROCEDURES

(71) Applicant: ArthroCare Corporation, Austin, TX (US)

(72) Inventors: David Y. Yuan, Cedar Park, TX (US); Jean Woloszko, Austin, TX (US); Jonathan L. Gaspredes, Austin, TX (US); Thomas P. Ryan, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 202 days.

(21) Appl. No.: 14/339,621

(22) Filed: Jul. 24, 2014

(65) Prior Publication Data

US 2016/0022350 A1    Jan. 28, 2016

(51) Int. Cl.
*A61B 18/12* (2006.01)
*A61B 18/04* (2006.01)
(Continued)

(52) U.S. Cl.
CPC ........ *A61B 18/1233* (2013.01); *A61B 18/042* (2013.01); *A61B 18/148* (2013.01);
(Continued)

(58) Field of Classification Search
CPC ...... A61B 18/1233; A61B 2018/00672; A61B 2018/00666; A61B 2018/00678;
(Continued)

(56) References Cited

U.S. PATENT DOCUMENTS 2,050,904 A   8/1936   Trice .............................. 219/233
2,275,167 A   3/1942   Bierman ......................... 606/50
(Continued)

FOREIGN PATENT DOCUMENTS

DE   2521719   11/1976   .............. A61N 3/02
DE   4425015   1/1996    ............. A61B 17/36
(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.
(Continued)

*Primary Examiner* — Jaymi Della
(74) *Attorney, Agent, or Firm* — David A. Warmbold

(57) ABSTRACT

Electrosurgical procedures. At least some of the example methods that include: supplying energy to an active electrode of an electrosurgical wand, the supplying energy to the active electrode by an electrosurgical controller; monitoring an electrical parameter associated with the energy; and determining, based on the electrical parameter, the presence of a wand condition of the electrosurgical wand, the wand condition being at least one selected from the group consisting of: a surface area of the active electrode is less than a predetermined threshold surface area; the surface area of the active electrode is approaching the predetermined threshold surface area; and that the electrosurgical wand is affected by a blockage.

16 Claims, 7 Drawing Sheets

(51) Int. Cl.
*A61B 18/00* (2006.01)
*A61B 18/14* (2006.01)

(52) U.S. Cl.
CPC .............. *A61B 2018/0066* (2013.01); *A61B 2018/00583* (2013.01); *A61B 2018/00672* (2013.01); *A61B 2018/00779* (2013.01); *A61B 2018/00791* (2013.01); *A61B 2018/00827* (2013.01); *A61B 2018/00863* (2013.01); *A61B 2018/00875* (2013.01); *A61B 2018/00892* (2013.01); *A61B 2018/00898* (2013.01); *A61B 2018/00988* (2013.01); *A61B 2018/122* (2013.01); *A61B 2018/1472* (2013.01); *A61B 2218/007* (2013.01); *A61B 2560/028* (2013.01); *A61B 2560/0276* (2013.01)

(58) Field of Classification Search
CPC A61B 2018/00863; A61B 2018/00869; A61B 2018/00875; A61B 2018/00827; A61B 2018/00892; A61B 2018/00791; A61B 2560/0276; A61B 2560/028
See application file for complete search history.

(56) References Cited

U.S. PATENT DOCUMENTS

| | | | |
|---|---|---|---|
| 3,699,967 A | 10/1972 | Anderson | 606/37 |
| 3,812,858 A | 5/1974 | Oringer | 604/22 |
| 3,945,375 A | 3/1976 | Banko | 600/104 |
| 4,033,351 A | 7/1977 | Hetzel | 606/48 |
| 4,203,444 A | 5/1980 | Bonnell et al. | 604/22 |
| 4,240,441 A | 12/1980 | Khalil | 128/692 |
| 4,269,174 A | 5/1981 | Adair | 128/842 |
| 4,411,266 A | 10/1983 | Cosman | 606/49 |
| 4,429,694 A | 2/1984 | McGreevy | 128/303.14 |
| 4,483,338 A | 11/1984 | Bloom et al. | 606/50 |
| 4,582,057 A | 4/1986 | Auth et al. | 606/31 |
| 4,641,649 A | 2/1987 | Walinsky | 606/33 |
| 4,674,499 A | 6/1987 | Pao | 606/50 |
| 4,709,698 A | 12/1987 | Johnston et al. | 128/303 |
| 4,719,914 A | 1/1988 | Johnson | 606/28 |
| 4,736,743 A | 4/1988 | Diakuzono | 128/303.1 |
| 4,737,678 A | 4/1988 | Hasegawa | 313/36 |
| 4,762,128 A | 8/1988 | Rosenbluth | 128/343 |
| 4,785,806 A | 11/1988 | Deckelbaum | 128/303.1 |
| 4,813,429 A | 3/1989 | Eshel et al. | 128/736 |
| 4,827,911 A | 5/1989 | Broadwin et al. | 604/22 |
| 4,860,752 A | 8/1989 | Turner | 128/422 |
| 4,903,696 A | 2/1990 | Stasz et al. | 606/37 |
| 4,940,064 A | 7/1990 | Desai | 607/122 |
| 4,955,377 A | 9/1990 | Lennox et al. | 128/401 |
| 4,968,314 A | 11/1990 | Michaels | 606/7 |
| 4,976,709 A | 12/1990 | Sand | 606/5 |
| 5,007,437 A | 4/1991 | Sterzer | 428/786 |
| 5,037,421 A | 8/1991 | Boutacoff et al. | 606/15 |
| 5,057,105 A | 10/1991 | Malone et al. | 606/28 |
| 5,057,106 A | 10/1991 | Kasevich et al. | 606/33 |
| 5,061,266 A | 10/1991 | Hakky | 606/15 |
| 5,083,565 A | 1/1992 | Parins | 128/642 |
| 5,084,045 A | 1/1992 | Helenowski | 606/32 |
| 5,092,339 A | 3/1992 | Geddes et al. | 128/692 |
| 5,093,877 A | 3/1992 | Aita et al. | 385/34 |
| 5,103,804 A | 4/1992 | Abele et al. | 600/116 |
| 5,137,530 A | 8/1992 | Sand | 606/5 |
| 5,147,354 A | 9/1992 | Boutacoff et al. | 606/15 |
| 5,151,098 A | 9/1992 | Loertscher | 606/16 |
| 5,176,528 A | 1/1993 | Fry et al. | 439/181 |
| 5,191,883 A | 3/1993 | Lennox et al. | 607/102 |
| 5,217,455 A | 6/1993 | Tan | 606/9 |
| 5,230,334 A | 7/1993 | Klopotek | 601/3 |
| 5,234,428 A | 8/1993 | Kaufman | 606/45 |
| 5,246,438 A | 9/1993 | Langberg | 606/33 |
| 5,249,585 A | 10/1993 | Turner et al. | 607/99 |
| 5,269,794 A | 12/1993 | Rexroth | 606/180 |
| 5,277,696 A | 1/1994 | Hagen | 606/49 |
| 5,293,868 A | 3/1994 | Nardella | 600/373 |
| 5,295,956 A | 3/1994 | Bales et al. | 604/30 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,318,563 A | 6/1994 | Malis et al. | 606/38 |
| 5,322,507 A | 6/1994 | Costello et al. | 128/4 |
| 5,330,518 A | 7/1994 | Neilson et al. | 607/101 |
| 5,334,183 A | 8/1994 | Wuchinich | 606/46 |
| 5,334,193 A | 8/1994 | Nardella | 606/41 |
| 5,335,668 A | 8/1994 | Nardella | 600/547 |
| 5,336,217 A | 8/1994 | Buys et al. | 606/9 |
| 5,336,220 A | 8/1994 | Ryan et al. | 604/22 |
| 5,348,554 A | 9/1994 | Imran et al. | 606/41 |
| 5,370,642 A | 12/1994 | Keller | 606/9 |
| 5,370,644 A | 12/1994 | Langberg | 606/33 |
| 5,374,265 A | 12/1994 | Sand | 606/5 |
| 5,395,363 A | 3/1995 | Billings et al. | 606/41 |
| 5,403,311 A | 4/1995 | Abele et al. | 606/49 |
| 5,405,376 A | 4/1995 | Mulier et al. | 607/127 |
| 5,423,803 A | 6/1995 | Tankovich | 606/9 |
| 5,423,844 A | 6/1995 | Miller | 606/171 |
| 5,431,649 A | 7/1995 | Mulier et al. | 606/41 |
| 5,433,708 A | 7/1995 | Nichols et al. | 604/113 |
| 5,437,664 A | 8/1995 | Cohen et al. | 606/42 |
| 5,445,634 A | 8/1995 | Keller | 606/9 |
| 5,458,596 A | 10/1995 | Lax et al. | 606/31 |
| 5,462,545 A | 10/1995 | Wang et al. | 606/41 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,505,710 A | 4/1996 | Dorsey, III | 604/158 |
| 5,520,685 A | 5/1996 | Wojciechowicz | 606/49 |
| 5,536,267 A | 7/1996 | Edwards et al. | 606/41 |
| 5,542,928 A | 8/1996 | Evans et al. | 604/113 |
| 5,545,161 A | 8/1996 | Imran | 606/41 |
| 5,562,703 A | 10/1996 | Desai | 606/210 |
| 5,579,764 A | 12/1996 | Goldreyer | 600/374 |
| 5,607,391 A | 3/1997 | Klinger et al. | 604/33 |
| 5,607,421 A | 3/1997 | Jeevanandam et al. | 606/15 |
| 5,626,576 A | 5/1997 | Janssen | 606/41 |
| 5,643,255 A | 7/1997 | Organ | 606/41 |
| 5,653,692 A | 8/1997 | Masterson et al. | 604/113 |
| 5,660,836 A | 8/1997 | Knowlton | 607/101 |
| 5,681,308 A | 10/1997 | Edwards et al. | 606/41 |
| 5,688,267 A | 11/1997 | Panescu et al. | 606/41 |
| 5,713,896 A | 2/1998 | Nardella | 606/50 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,769,843 A | 6/1998 | Abela et al. | 606/10 |
| 5,769,847 A | 6/1998 | Panescu et al. | 606/42 |
| 5,782,795 A | 7/1998 | Bays | 604/22 |
| 5,785,705 A | 7/1998 | Baker | 606/32 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,810,802 A | 9/1998 | Panescu et al. | 606/31 |
| 5,843,078 A | 12/1998 | Sharkey | 606/41 |
| 5,855,277 A | 1/1999 | Apps et al. | 606/35 |
| 5,871,524 A | 2/1999 | Knowlton | 607/101 |
| 5,876,398 A | 3/1999 | Mulier et al. | 606/41 |
| 5,893,848 A | 4/1999 | Negus et al. | 606/41 |
| 5,895,386 A | 4/1999 | Odell et al. | 606/50 |
| 5,904,681 A | 5/1999 | West, Jr. | 606/41 |
| 5,906,613 A | 5/1999 | Mulier et al. | 606/41 |
| 5,919,219 A | 7/1999 | Knowlton | 607/102 |
| 5,964,754 A | 10/1999 | Osypka | 606/37 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,007,533 A | 12/1999 | Casscells et al. | 606/45 |
| 6,007,570 A | 12/1999 | Sharkey et al. | 607/96 |

(56) References Cited

U.S. PATENT DOCUMENTS

| | | | |
|---|---|---|---|
| 6,016,809 A | 1/2000 | Mulier et al. | 128/898 |
| 6,030,383 A | 2/2000 | Benderev | 606/45 |
| 6,032,673 A | 3/2000 | Savage et al. | 128/898 |
| 6,032,674 A | 3/2000 | Eggers et al. | 606/41 |
| 6,042,580 A | 3/2000 | Simpson | 606/32 |
| 6,045,532 A | 4/2000 | Eggers et al. | 604/114 |
| 6,053,172 A | 4/2000 | Hovda et al. | 128/898 |
| 6,063,081 A | 5/2000 | Mulier et al. | 606/41 |
| 6,091,995 A | 7/2000 | Ingle et al. | 607/138 |
| 6,096,037 A | 8/2000 | Mulier et al. | 606/49 |
| 6,110,169 A | 8/2000 | Mueller et al. | 606/48 |
| 6,152,923 A | 11/2000 | Ryan | 606/51 |
| 6,156,031 A | 12/2000 | Aita et al. | 606/33 |
| 6,210,405 B1 | 4/2001 | Goble et al. | 606/41 |
| 6,214,001 B1 | 4/2001 | Casscells et al. | 606/41 |
| 6,217,575 B1 | 4/2001 | DeVore et al. | 606/41 |
| 6,235,022 B1 | 5/2001 | Lee et al. | 606/41 |
| 6,238,393 B1 | 5/2001 | Mulier et al. | 607/127 |
| 6,264,650 B1 | 7/2001 | Hovda et al. | 606/32 |
| 6,267,757 B1 | 7/2001 | Aita et al. | 606/33 |
| 6,283,961 B1 | 9/2001 | Underwood et al. | 606/41 |
| 6,302,903 B1 | 10/2001 | Mulier et al. | 607/105 |
| 6,312,429 B1 | 11/2001 | Burbank et al. | 606/47 |
| 6,315,774 B1 | 11/2001 | Daniel et al. | 606/15 |
| 6,322,494 B1 | 11/2001 | Bullivant et al. | 600/104 |
| 6,325,799 B1 | 12/2001 | Goble | 606/41 |
| 6,327,505 B1 | 12/2001 | Medhkour et al. | 607/99 |
| 6,328,736 B1 | 12/2001 | Mulier et al. | 606/45 |
| 6,336,926 B1 | 1/2002 | Goble | 606/34 |
| 6,346,107 B1 | 2/2002 | Cucin | 606/49 |
| 6,355,006 B1 | 3/2002 | Ryaby et al. | 601/2 |
| 6,358,248 B1 | 3/2002 | Mulier et al. | 606/41 |
| 6,379,350 B1 | 4/2002 | Sharkey et al. | 606/41 |
| 6,391,028 B1 | 5/2002 | Fanton et al. | 606/45 |
| 6,398,781 B1 | 6/2002 | Goble et al. | 606/41 |
| 6,409,724 B1 | 6/2002 | Penny et al. | 606/41 |
| 6,432,105 B1 | 8/2002 | Ellman et al. | 606/48 |
| 6,482,202 B1 | 11/2002 | Goble et al. | 606/41 |
| 6,491,690 B1 | 12/2002 | Goble et al. | 606/41 |
| 6,497,705 B2 | 12/2002 | Comben | 606/41 |
| 6,497,706 B2 | 12/2002 | Burbank et al. | 606/45 |
| 6,510,854 B2 | 1/2003 | Goble | 128/898 |
| 6,514,250 B1 | 2/2003 | Jahns et al. | 606/41 |
| 6,517,535 B2 | 2/2003 | Edwards | 606/41 |
| 6,540,741 B1 | 4/2003 | Underwood et al. | 606/32 |
| 6,557,559 B1 | 5/2003 | Eggers et al. | 128/898 |
| 6,575,968 B1 | 6/2003 | Eggers et al. | 606/41 |
| 6,575,969 B1 | 6/2003 | Rittman, III et al. | 606/41 |
| 6,582,423 B1 | 6/2003 | Thapliyal et al. | 606/32 |
| 6,595,990 B1 | 7/2003 | Weinstein et al. | 606/41 |
| 6,597,950 B2 | 7/2003 | Linder et al. | 607/8 |
| 6,605,085 B1 | 8/2003 | Edwards | 606/41 |
| 6,610,059 B1 | 8/2003 | West, Jr. | 606/41 |
| 6,632,230 B2 | 10/2003 | Barry | 606/159 |
| 6,645,203 B2 | 11/2003 | Sharkey et al. | 606/41 |
| 6,663,628 B2 | 12/2003 | Peters | 606/45 |
| 6,695,839 B2 | 2/2004 | Sharkey et al. | 606/49 |
| 6,699,206 B2 | 3/2004 | Burbank et al. | 606/567 |
| 6,699,244 B2 | 3/2004 | Carranza et al. | 606/41 |
| 6,702,810 B2 | 3/2004 | McClurken et al. | 606/34 |
| 6,746,447 B2 | 6/2004 | Davison et al. | 606/41 |
| 6,763,836 B2 | 7/2004 | Tasto et al. | 128/898 |
| 6,796,982 B2 | 9/2004 | Carmel et al. | 606/41 |
| 6,805,130 B2 | 10/2004 | Tasto et al. | 606/32 |
| 6,827,725 B2 | 12/2004 | Batchelor et al. | 606/170 |
| 6,832,996 B2 | 12/2004 | Woloszko et al. | 606/41 |
| 6,855,143 B2 | 2/2005 | Davison et al. | 606/41 |
| 6,896,674 B1 | 5/2005 | Woloszko et al. | 606/41 |
| 6,904,303 B2 | 6/2005 | Phan et al. | 600/374 |
| 6,979,332 B2 | 12/2005 | Adams | 606/45 |
| 7,150,747 B1 | 12/2006 | McDonald et al. | 606/45 |
| 7,184,811 B2 | 2/2007 | Phan et al. | 600/374 |
| 7,258,690 B2 | 8/2007 | Sutton et al. | 606/45 |
| 7,261,712 B2 | 8/2007 | Burbank et al. | 606/49 |
| 7,429,262 B2 | 9/2008 | Woloszko et al. | 606/48 |
| 7,488,295 B2 | 2/2009 | Burbank et al. | 606/167 |
| 7,776,034 B2 | 8/2010 | Kampa | 606/41 |
| 7,819,863 B2 | 10/2010 | Eggers et al. | 606/32 |
| 8,038,670 B2 | 10/2011 | McClurken | 606/41 |
| 8,317,786 B2 | 11/2012 | Dahla et al. | 606/48 |
| 8,323,279 B2 | 12/2012 | Dahla et al. | 606/48 |
| 8,355,799 B2 | 1/2013 | Marion et al. | 607/102 |
| 8,747,400 B2 | 6/2014 | Bigley et al. | 606/41 |
| 2002/0049438 A1 | 4/2002 | Sharkey et al. | 606/41 |
| 2002/0072739 A1 | 6/2002 | Lee et al. | 606/47 |
| 2003/0036753 A1 | 2/2003 | Morgan et al. | 606/32 |
| 2003/0097129 A1 | 5/2003 | Davison et al. | 606/41 |
| 2003/0130711 A1 | 7/2003 | Pearson et al. | 607/101 |
| 2004/0030330 A1 | 2/2004 | Brassell et al. | 606/41 |
| 2007/0149965 A1 | 6/2007 | Gallo et al. | 606/41 |
| 2008/0021447 A1 | 1/2008 | Davison et al. | 606/41 |
| 2008/0167645 A1* | 7/2008 | Woloszko | A61B 18/1206 606/40 |
| 2008/0167646 A1 | 7/2008 | Godara et al. | 606/41 |
| 2008/0234673 A1 | 9/2008 | Marion et al. | 606/45 |
| 2008/0300590 A1 | 12/2008 | Horne et al. | 606/35 |
| 2009/0138011 A1 | 5/2009 | Epstein | 606/42 |
| 2009/0209958 A1 | 8/2009 | Davison et al. | 606/41 |
| 2010/0042095 A1 | 2/2010 | Bigley et al. | 606/41 |
| 2010/0204690 A1 | 8/2010 | Bigley et al. | 606/41 |
| 2011/0270242 A1 | 11/2011 | Marion | 606/35 |
| 2012/0179157 A1 | 7/2012 | Frazier et al. | 606/41 |
| 2013/0116689 A1 | 5/2013 | Marion | 606/42 |
| 2014/0155883 A1 | 6/2014 | Marion | 606/34 |
| 2014/0155884 A1 | 6/2014 | Marion | 606/35 |

FOREIGN PATENT DOCUMENTS

| | | | |
|---|---|---|---|
| DE | 296 09 350 | 8/1996 | A61B 17/39 |
| DE | 195 37 084 | 4/1997 | A61B 17/36 |
| DE | 296 19 029 | 4/1997 | A61B 17/34 |
| DE | 19850671 | 5/1999 | A61B 17/22 |
| DE | 10254668 | 6/2004 | A61B 18/12 |
| DE | 69822877 | 1/2005 | A61B 17/20 |
| DE | 202008000276 | 6/2008 | A61B 18/12 |
| DE | 102009057921 A1 | 6/2010 | A61B 18/12 |
| EP | 0 502 268 | 9/1992 | A61B 17/39 |
| EP | 0 515 867 | 12/1992 | A61B 17/36 |
| EP | 543123 | 5/1993 | A61B 17/39 |
| EP | 0 597 463 | 5/1994 | A61N 5/04 |
| EP | 774926 | 3/1995 | A61B 17/39 |
| EP | 0 650 701 | 5/1995 | A61B 17/39 |
| EP | 923907 | 6/1999 | A61B 17/39 |
| EP | 1149564 | 10/2001 | A61B 18/14 |
| EP | 1041933 | 3/2004 | A61B 17/20 |
| GB | 2037167 | 7/1980 | A61B 17/36 |
| GB | 2331247 | 5/1999 | A61B 17/39 |
| GB | 2379878 | 3/2003 | A61B 18/04 |
| GB | 2408936 | 6/2005 | A61B 18/14 |
| JP | 57-183850 | 11/1982 | A61F 9/00 |
| JP | 63-40099 | 8/1988 | A61B 17/39 |
| JP | 9-501328 | 2/1997 | A61B 17/39 |
| WO | 91/13650 | 9/1991 | A61N 5/04 |
| WO | 94/03134 | 2/1994 | A61B 18/20 |
| WO | 94/10924 | 5/1994 | A61B 17/39 |
| WO | 94/14383 | 7/1994 | A61B 17/36 |
| WO | 94/26228 | 11/1994 | A61G 17/36 |
| WO | 95/05780 | 3/1995 | A61B 17/36 |
| WO | 95/05781 | 3/1995 | A61B 17/39 |
| WO | 95/05867 | 3/1995 | A61N 1/05 |
| WO | 95/10326 | 4/1995 | A61N 5/00 |
| WO | 95/30373 | 11/1995 | A61B 17/00 |
| WO | 96/07360 | 3/1996 | A61B 17/39 |
| WO | 96/34568 | 11/1996 | A61B 17/36 |
| WO | 96/35469 | 11/1996 | A61B 17/36 |
| WO | 96/39914 | 12/1996 | A61B 1/00 |
| WO | 96/39962 | 12/1996 | A61B 17/36 |
| WO | 96/39964 | 12/1996 | A61B 17/36 |
| WO | 96/39965 | 12/1996 | A61B 17/36 |
| WO | 96/39967 | 12/1996 | A61B 17/38 |
| WO | 97/15238 | 5/1997 | A61B 17/39 |
| WO | 97/18765 | 5/1997 | A61B 17/36 |
| WO | 97/24992 | 7/1997 | A61B 17/38 |
| WO | 97/25101 | 7/1997 | A61N 5/00 |

(56) References Cited

FOREIGN PATENT DOCUMENTS

| | | | |
|---|---|---|---|
| WO | 97/32551 | 9/1997 | ............ A61F 11/00 |
| WO | 97/33523 | 9/1997 | ............ A61B 17/32 |
| WO | 97/34540 | 9/1997 | ............ A61B 17/36 |
| WO | 97/41786 | 11/1997 | ............ A61B 17/39 |
| WO | 97/44071 | 11/1997 | ............ A61M 1/10 |
| WO | 98/14131 | 4/1998 | ............ A61B 18/14 |
| WO | 98/17185 | 4/1998 | ............ A61B 17/36 |
| WO | 98/17186 | 4/1998 | ............ A61B 17/36 |
| WO | 98/27877 | 7/1998 | ............ A61B 17/32 |
| WO | 98/30144 | 7/1998 | ............ A61B 17/36 |
| WO | 98/34550 | 8/1998 | ............ A61B 17/39 |
| WO | 98/34558 | 8/1998 | ............ A61B 18/00 |
| WO | 98/38925 | 9/1998 | ............ A61B 17/20 |
| WO | 98/39038 | 9/1998 | ............ A61M 5/00 |
| WO | 99/00060 | 1/1999 | ............ A61B 17/22 |
| WO | 99/20185 | 4/1999 | ............ A61B 17/20 |
| WO | 99/42037 | 8/1999 | ............ A61B 17/00 |
| WO | 99/44506 | 9/1999 | ............ A61B 10/00 |
| WO | 00/09053 | 2/2000 | ............. A61F 7/12 |
| WO | 01/26570 | 4/2001 | ............ A61B 18/14 |
| WO | 01/95819 | 12/2001 | ............ A61B 18/14 |
| WO | 02/78557 | 10/2002 | ............ A61B 18/18 |
| WO | 03/024339 | 3/2003 | ............ A61B 17/32 |
| WO | 2008/073727 | 6/2008 | ............ A61B 18/14 |
| WO | 2009/094392 | 7/2009 | ............ A61B 18/14 |
| WO | 2011/071482 | 6/2011 | ............ A61B 18/14 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.

Hardy et al., "Regional Myocardial Blood Flow and Cardiac mechanics in dog Hearts with CO2 laser-induced Intramyocardial Revascularization", Basic Research in cardiology 85:179-196 (1990).

Mirhoseini et al., "New Concepts in Revascularization of the Myocardium", Ann Thorac Surg 45:415-420 (1988).

Mirhoseini et al., "Revascularization of the heart by Laser", J. of Microsurgery 2:253-260 (1981).

Mirhoseini et al., "Transmyocardial Laser Revascularization: A Review", J. of Clinical Laser medicine & Surgery 11 (1) :15-19 (1993).

Mirhoseini et al., "Transventricular Revascularization by Laser", Lasers in Surgery and Medicine 2:187-198 (1982).

Rand et al., "Effect of Elecctrocautery on Fresh Human Articular Cartilage", J. Arthro. Surg., vol. 1, pp. 242-246, 1985.

Walter et al., "Treatment of Acute Mycardial Infarction by Transmural Blood Supply from the Ventricular Cavity", Erop. Surgery Res. 3:130-138 (1971).

Whittaker et al., "Transmural Channels Can Protect Ischemic Tissue", Circulation 93(1):143-152 Jan. 1, 1996.

EP Search Report for EP01124768 2 pgs Nov. 30, 2001.
EP Search Report for EP01935650 10 pgs Mailed Jul. 26, 2006.
EP Search Report for EP01935650 8 pgs Mailed May 3, 2005.
EP Search Report for EP02768969 3 pgs Mailed Feb. 12, 2007.
EP Search Report for EP03762238 3 pgs Mailed Jun. 2, 2006.
EP Search Report for EP94916716 2 pgs Oct. 29, 1996.
EP Search Report for EP96941386 2 pgs Nov. 27, 1998.
EP Search Report for EP98952032 2 pgs Nov. 24, 2000.
EP Search Report for EP 03736488 3 pgs Mailed Jun. 25, 2009.
EP Search Report for EP 07118068 3pgs Mailed Dec. 27, 2010.
EP Search Report for EP 04778347 4pgs Feb. 22, 2011.
PCT International Search Report for PCT/US00/07718 1pg Mailed Sep. 5, 2000.
PCT International Search Report for PCT/US01/16006 1pg Mailed Aug. 14, 2001.
PCT International Search Report for PCT/US02/31640 1pg Mailed May 23, 2003.
PCT International Search Report for PCT/US03/04689 1pg Mailed Sep. 26, 2003.
PCT International Search Report for PCT/US03/12790 1pg Mailed Aug. 12, 2003.
PCT International Search Report for PCT/US03/20574 1pg Mailed May 25, 2005.
PCT International Search Report for PCT/US04/22803 1pg Mailed Apr. 29, 2005.
PCT International Search Report for PCT/US05/07038 1pg Mailed Sep. 2, 2005.
PCT International Search Report for PCT/US94/05168, 1 pg Mailed Oct. 18, 1994.
PCT International Search Report for PCT/US96/18505, 3 pgs Mailed Jan. 17, 1997.
PCT International Search Report for PCT/US98/20768 1pg Mailed Jan. 20, 1999.
PCT International Search Report for PCT/US98/22327 1pg Mailed Feb. 9, 1999.
PCT Notif of the Int'l Search Report and Written Opinion for PCT/US09/67001 6 pgs; Mailed Jan. 29, 2010.
PCT IPER for PCT/US01/16006 3pgs Apr. 16, 2002.
PCT IPER for PCT/US98/22327 4pgs Aug. 27, 2000.
PCT Written Opinion for PCT/US04/22803 3pgs Mailed Apr. 29, 2005.
PCT Written Opinion for PCT/US05/07038 3pgs Mailed Sep. 2, 2005.
UK Search Report for GB0805061.9 1 pg. Jul. 15, 2008.
UK Search Report for GB0921635.9 3pgs Apr. 12, 2010.
K Search Report for GB1106425.0 6 pages, Aug. 16, 2011.
UK combined Search and Examination Report for GB1121048.1 3pgs, Apr. 18, 2012.

* cited by examiner

METHOD AND SYSTEM RELATED TO ELECTROSURGICAL PROCEDURES

CROSS-REFERENCE TO RELATED APPLICATIONS

None.

BACKGROUND

Electrosurgical systems are used by physicians to remove several different tissue types. For example, procedures involving the knee or shoulder may remove portions of cartilage, meniscus, and free floating and/or trapped tissue. In some cases, the removal may be a very slight removal, such as tissue sculpting, and in other cases the more aggressive removal of tissue is used. Removing each different tissue type, and/or aggressiveness, may represent a different amount of applied energy.

Electrosurgical wands used with electrosurgical systems in electrosurgical procedures have a limited useful life. Any advance that makes determining when an electrosurgical wand has reached the end of its useful life and/or fluid flow through the wand has been at least partially blocked during an electrosurgical procedure would enable surgeons to plan more effectively and/or take corrective action.

BRIEF DESCRIPTION OF THE DRAWINGS

For a detailed description of exemplary embodiments, reference will now be made to the accompanying drawings in which.

NOTATION AND NOMENCLATURE

Figure 1:
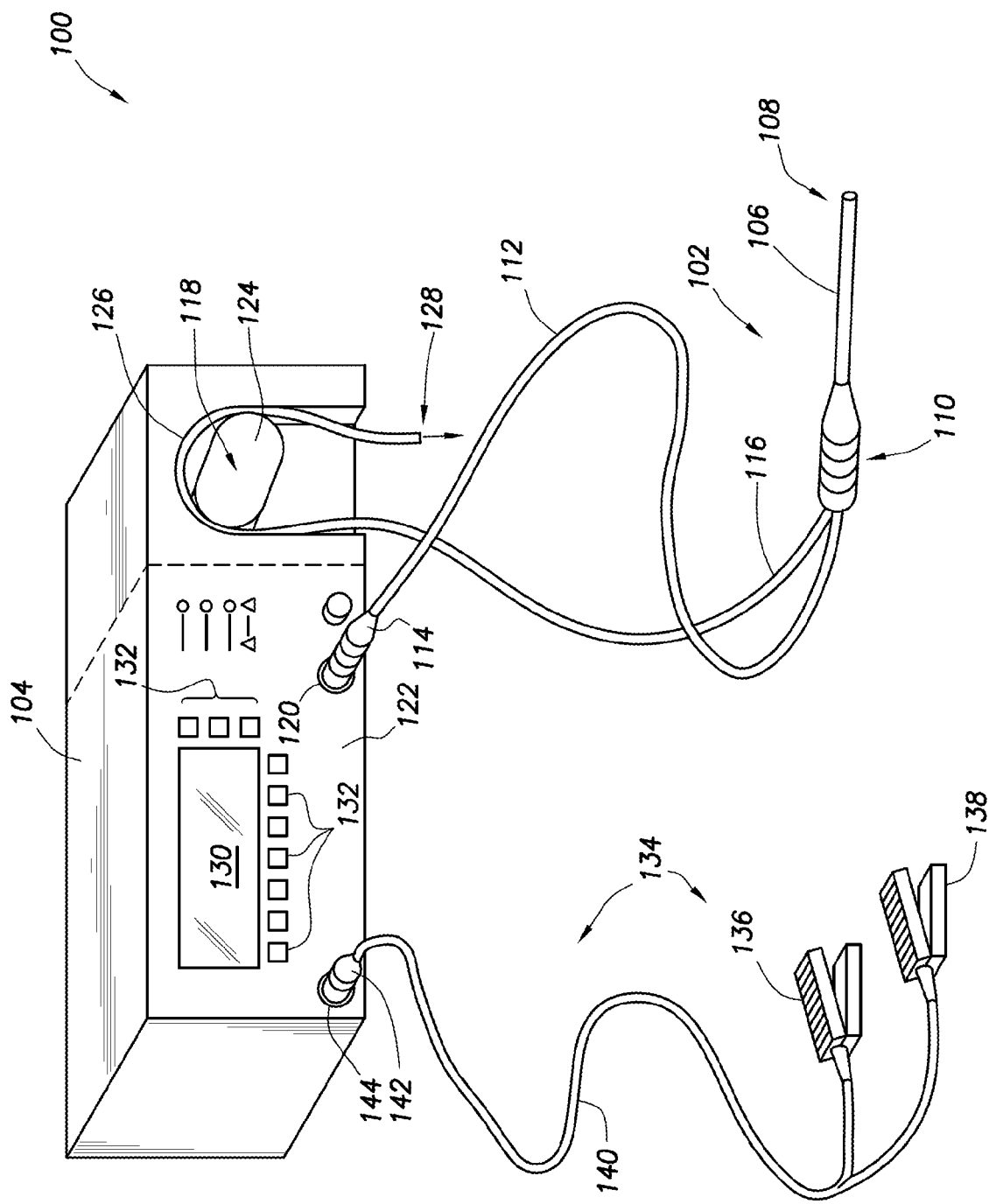
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Mode of ablation" shall refer to one or more characteristics of an ablation. Lack of ablation (i.e., a lack of plasma) shall not be considered a "mode of ablation." A mode which performs coagulation shall not be considered a "mode of ablation."

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Electric motor" shall include alternating current (AC) motors, direct current (DC) motors, as well as stepper motors.

"Controlling flow of fluid" shall mean controlling a volume flow rate. Control of applied pressure to maintain a set point pressure (e.g., suction pressure) independent of volume flow rate of liquid caused by the applied pressure shall not be considered "controlling flow of fluid." However, varying applied pressure to maintain a set point volume flow rate of liquid shall be considered "controlling flow of fluid".

"Energy range" shall refer to a lower limit energy, upper limit energy, and all the intervening energies between the lower limit and the upper limit. A first energy range and a second energy range may overlap (e.g., the lower limit of the second energy range may be an intervening energy in the first energy range), but so long as at least a portion of each energy range is mutually exclusive, the two energy ranges shall be considered distinct for purposes of the specification and claims.

"Energy setpoint" shall refer to a specific energy that falls within an energy range.

"Impedance" shall mean complex impedance (or any portion thereof, e.g., the real portion, the imaginary portion) of an electrode circuit, including the plasma created and maintained in operational relationship to an active electrode of a wand, fluid between the active and return electrode, and the electrode-fluid interface.

A proximity that is in "operational relationship with tissue" shall mean a proximity wherein the tissue interacting with a plasma affects the impedance presented by the plasma to electrical current flow through the plasma.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems. In particular, example embodiments are directed to an electrosurgical system that has the ability to monitor the active electrode of an electrosurgical wand, to determine in real-time (during use of the electrosurgical wand) that the active electrode is approaching or exceeded the active electrode's useful life and/or to detect a clog condition, and to provide an indication or warning. The various embodiments are discussed first in the context of useful life detection, but as will be discussed more below the same techniques can be used for clog detection. Moreover, the various embodiments of determining the state of the useful life of the active electrode may be implemented with electrosurgical controllers that have multiple modes of ablation with varying amounts of applied energy. The specification first turns to an illustrative system to orient the reader.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to the externally accessible tubular members. As illustrated, the wand 102 has a flexible tubular member 116, used to provide aspiration at the distal end 108 of the wand. In accordance with example systems, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure) (e.g., bolted to the outside of the enclosure), but in any event the peristaltic pump may be operatively coupled to the controller 104.

The example peristaltic pump 118 comprises a rotor portion 124 (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-roller rotor 124, varying types of peristaltic pumps 118 may be used (e.g., a five-roller peristaltic pump). In other example systems, the tubing 116 may couple to any source of vacuum, such as a vacuum source available in most hospital and/or surgical centers.

Still referring to FIG. 1, a display device or interface device 130 is visible through the enclosure 122 of the controller 104. The example interface device 130 may be used select operational modes of the controller 104 (either directly on the interface device 130 or by way of related buttons 132), and the interface device 130 may also be the location where information is provided to the surgeon. For example, the interface device 130 may display an indication that the active electrode of the wand 102 is approaching, has reached, or has exceeded the useful life of the active electrode. Various aspects of determining the state of the useful life of the electrode are discussed in more detail below.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102, and more specifically for control of energy in a mode of ablation. Further, pedal device 138 may be used to control and/or set the mode of ablation of the electrosurgical system. For example, actuation of pedal device 138 may switch between energy levels created by the controller 104 and aspiration volume created by the peristaltic pump 118. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may have a variety of modes of ablation which employ Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. N. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; the temperature of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of ablation does not ablate such fatty tissue; however, the Coblation® technology at the lower energy levels may be used to effectively ablate cells to release the inner fat content in a liquid form. Other modes of ablation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 2:
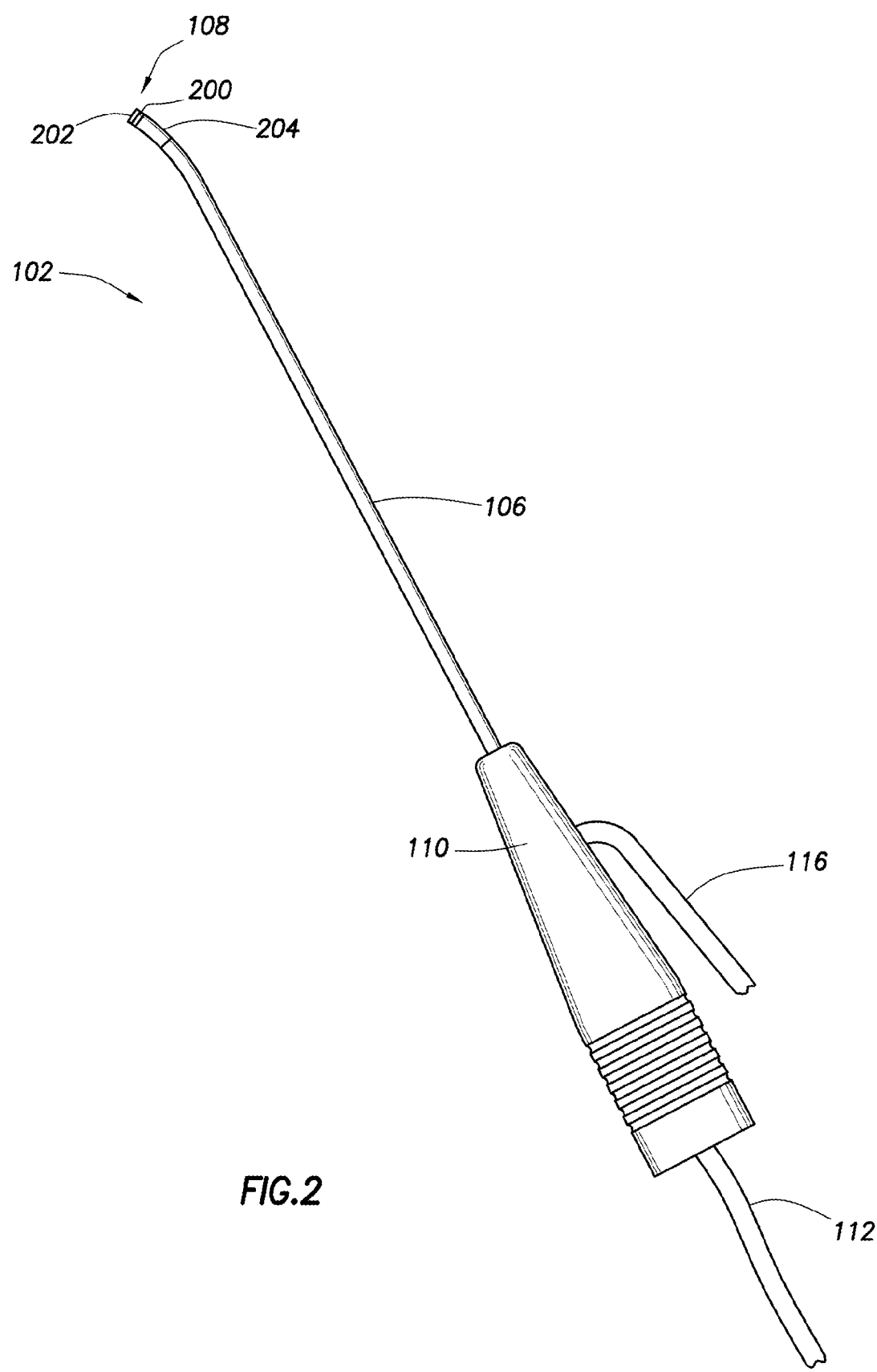
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106, and an electrode support member 200 coupled to the distal end of elongate shaft 106. Also visible in FIG. 2 is the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors (not shown) in the multi-conductor cable 112. The active electrode 202 is electrically isolated from a common or return electrode 204 which is disposed on the shaft proximal of the active electrode 202, in some example systems within 1 millimeter (mm) to 25 mm of the distal tip. Proximally from the distal tip, the return electrode 204 located along the elongate shaft 106 of the wand 102. The support member 200 is positioned distal to the return electrode 204 and may be composed of an electrically insulating material such as epoxy, plastic, ceramic, silicone, glass or the like. Support member 200 extends from the distal end 108 of elongate shaft 106 (usually about 1 to 20 mm) and provides support for active electrode 202.

Figure 3:
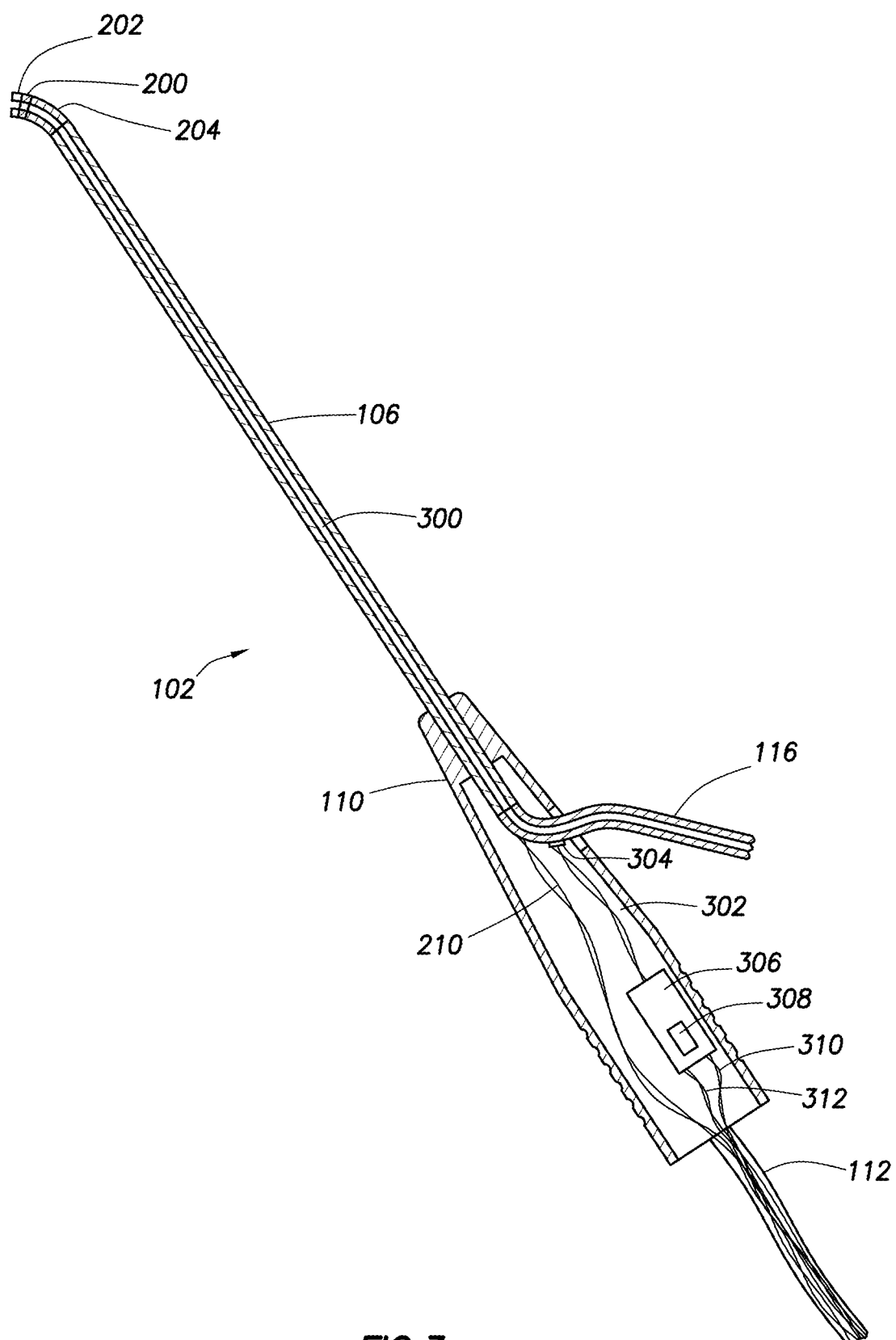
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 300 defined within the elongate shaft 106. In the example wand 102 of FIG. 3, the inside diameter of the elongate shaft 106 defines the suction lumen 300, but in other cases a separate tubing within the elongate shaft 106 may define the suction lumen 300. The suction lumen 300 may be used for aspirating excess fluids, bubbles, tissue fragments, and/or products of ablation from the target site through one or more apertures in or around the active electrode 202. Suction lumen 300 extends into the handle 110 and fluidly couples to the flexible tubular member 116 for coupling to the peristaltic pump 118 (FIG. 1) or other source of aspiration suction. Handle 110 also defines an inner cavity 302 within which electrical conductors 210 may reside, where the electrical conductors 210 may extend into the multi-conductor cable 112 and ultimately couple to the controller 104 (FIG. 1). The electrical conductors 210 likewise extend through the elongate shaft and couple, one each, to the return electrode 204 and the active electrode 202, but the electrical conductors 210 are not shown to reside within the elongate shaft 106 so as not to unduly complicate the figure.

In some systems, the wand 102 may further comprise a temperature measurement device positioned to measure a temperature associated with the fluid drawn in from the vicinity of the active electrode. In the example system of FIG. 3, temperature measurement device 304 is in operational relationship to the flexible tubular member 116. As illustrated in FIG. 3, the temperature measurement device resides within the inner cavity 302 defined by the handle 110, but the temperature measurement device may be placed at any suitable location. As illustrated, the temperature measurement device 304 abuts an outer surface of the tubular member 116 such that as fluids travel within the tubular member 116 past the location of the temperature measurement device 304, localized temperature changes can be read. The temperature measurement device 304 may take any suitable form, such as a resistive thermal device (RTD), a thermistor, an optical temperature probe, or a thermocouple. Temperature measured by the temperature measurement device 304 may be useful in a variety of operational circumstances, such as part of the determination of state of the useful life of the active electrode 202 and/or clog detection, both of which are discussed more below.

Still referring to FIG. 3, in example systems the wand 102 may have processor 306 disposed within inner cavity 302. The processor 302 may be a microcontroller from any of a variety of available sources, such as one of the many microcontrollers available from Freescale Semiconductors, Inc. of Austin, Tex. The processor 302 may have onboard non-volatile memory 308 within which various programs and data may be stored. In example systems, the non-volatile memory 308 may store a program that, when executed by the processor, causes the processor 306 to periodically read temperature measurement device 304 (electrically coupled to the processor 306) and then digitally send the temperature values to the controller 104 by way of conductors 310. The processor 306 may be powered from the controller 104 through the multi-conductor cable 112, such as by conductors 312. The non-volatile memory 308 may also store parameters associated with the determinations regarding useful life of the active electrode 202, which parameters are discussed in greater detail below.

In yet still further cases, the temperature measurement device may be associated with the suction lumen 300. For example, the assignee of the current specification has a technology directed to a temperature measurement device on the elongate shaft 106 proximal of the return electrode 204. Such a temperature measurement device may be primarily responsive to the temperature surrounding the elongate shaft 106, but such location for the temperature measurement device would also make the device secondarily responsive to temperature of fluid drawn into the suction lumen 300 from the vicinity of the active electrode. Thus, temperature measurements closer to the active electrode may also be used alone or in combination with the temperature measurement device 304 for the temperature aspects of the various embodiments. Reference is also made to commonly assigned U.S. Pat. No. 8,696,659, entitled "ELECTROSURGICAL SYSTEM AND METHOD HAVING ENHANCED TEMPERATURE MEASUREMENT", the complete disclosure of which is incorporated herein by reference as if reproduced in full below.

Figure 4:
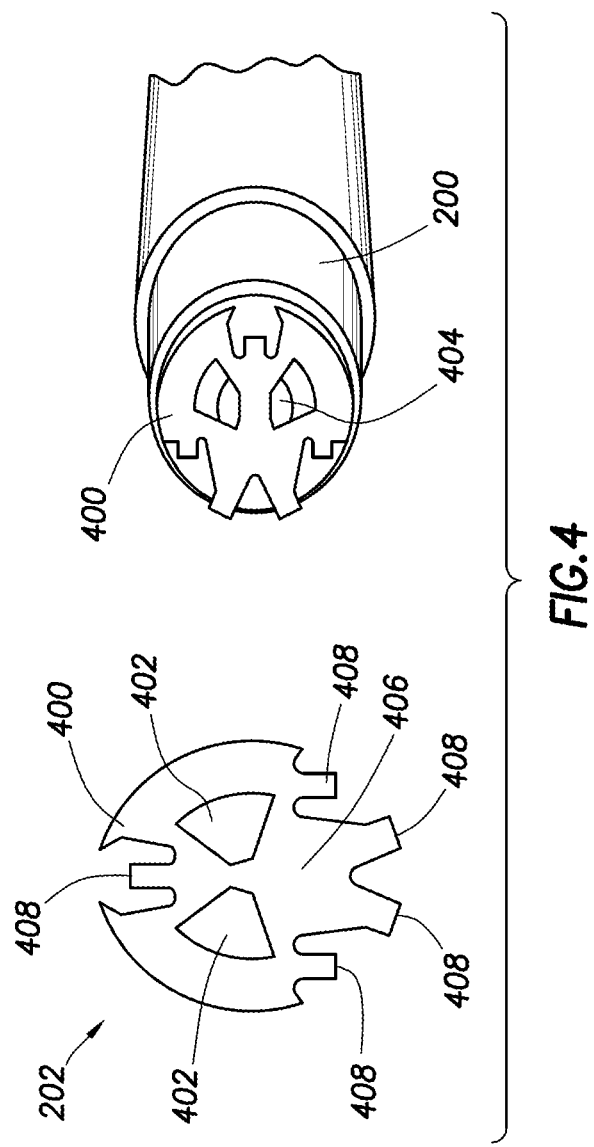
FIG. 4 shows both an elevation view an active electrode and a perspective view of the distal end of a wand (including the active electrode) in accordance with at least some embodiments.

FIG. 4 shows an elevation view of an example active electrode (on the left), as well as a perspective view of the distal end of wand 102 (on the right), in accordance with example systems. In particular, active electrode 202 may be an active screen electrode 400 as shown in FIG. 4. Screen electrode 400 may comprise a conductive material, such as tungsten, titanium, molybdenum, platinum, or the like. Prior to the first use, screen electrode 400 may have a diameter in the range of about 0.5 to 8 mm, in some cases about 1 to 4 mm, and a thickness of about 0.05 to about 2.5 mm, in some cases about 0.1 to 1 mm. Screen electrode 400 may comprise a plurality of apertures 402 configured to rest over an aperture or distal opening 404 of the suction lumen. Apertures 402 enable the passage of aspirated excess fluids, bubbles, and gases from the ablation site, and the apertures 402 are large enough to enable ablated tissue fragments to pass through into suction lumen 300 (FIG. 3). As shown, screen electrode 400 has an irregular shape which increases the edge to surface-area ratio of the screen electrode 400. A large edge to surface-area ratio increases the ability of screen electrode 400 to initiate and maintain a plasma layer in conductive fluid because the edges generate higher current densities, which a large surface area electrode tends to dissipate power into the conductive media.

In the representative embodiment shown in FIG. 4, screen electrode 400 comprises a body 406 that rests over insulative support member 200 and the distal opening 404 to suction lumen 300. Screen electrode 400 further comprises tabs 408, in the example screen electrode 400 of FIG. 4, five tabs 408 are shown. The tabs 408 may rest on, be secured to, and/or be embedded in insulative support member 200. In certain embodiments, electrical connectors extend through insulative support member 200 and are coupled (i.e., via adhesive, braze, weld, or the like) to one or more of tabs 408 in order to secure screen electrode 400 to the insulative support member 200 and to electrically couple screen electrode 400 to controller 104 (FIG. 1). In example systems, screen electrode 400 forms a substantially planar tissue treatment surface for smooth resection, ablation, and sculpting of the meniscus, cartilage, and other tissues. In reshaping cartilage and meniscus, the physician often desires to smooth the irregular and ragged surface of the tissue, leaving behind a substantially smooth surface. For these applications, a substantially planar screen electrode treatment surface provides the desired effect. The specification now turns to a more detailed description of the controller 104.

Figure 5:
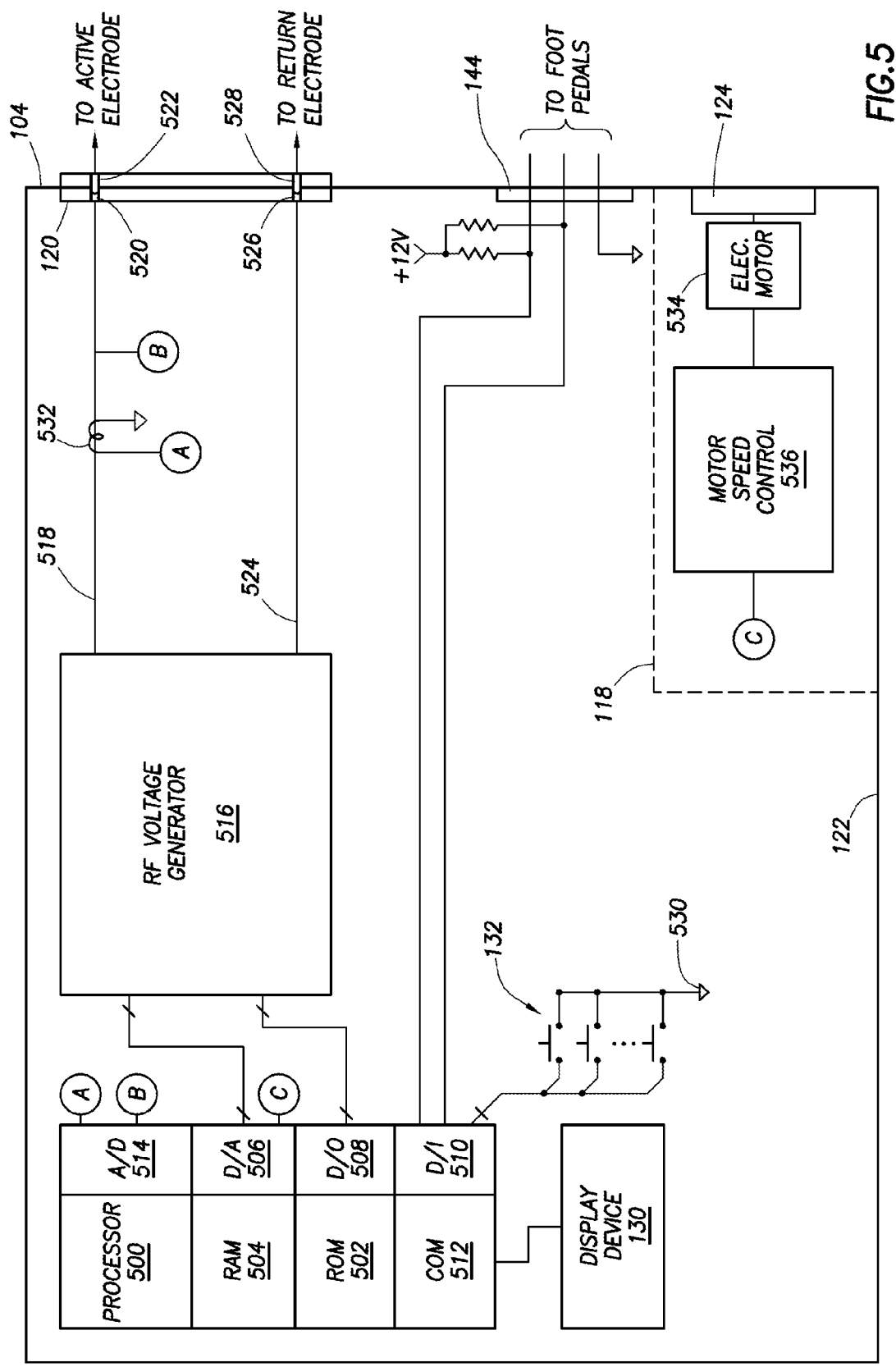
FIG. 5 shows a block diagram of an electrosurgical controller in accordance with at least some embodiments.

FIG. 5 shows an electrical block diagram of controller 104 in accordance with example systems. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, analog-to-digital converter (A/D) 514, digital outputs (D/O) 508, and digital inputs (D/I) 510. The processor 500 may further provide one or more externally available peripheral busses, such as a serial bus (e.g., $I_2C$), parallel bus, or other bus and corresponding communication mode. The processor 500 may further be integral with communication logic 512 to enable the processor 500 to communicate with external devices, as well as internal devices, such as display device 130. Although in some embodiments the processor 500 may be implemented in the form of a microcontroller, in other embodiments the processor 500 may be implemented as a standalone central processing unit in combination with individual RAM, ROM, communication, A/D, D/A, D/O, and D/I devices, as well as communication hardware for communication to peripheral components.

ROM 502 stores instructions executable by the processor 500. In particular, the ROM 502 may comprise a software program that, when executed, causes the controller to determine the presence or absence of various wand conditions, such as the active electrode of the wand 102 approaching, reaching, or exceeding the useful life of the active electrode. Similarly, the program, when executed, causes the controller to determine the presence or absence of a clog associated with the wand 102. The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF voltage generator 516), digital outputs 508 (e.g., in some embodiment the RF voltage generator 516), digital inputs 510 (e.g., interface devices such as push button switches 132 or foot pedal assembly 134 (FIG. 1)), and communication device 512 (e.g., display device 130).

Voltage generator 516 generates an alternating current (AC) voltage signal that is coupled to active electrode 202 of the wand 102 (FIG. 3). In some embodiments, the voltage generator defines an active terminal 518 which couples to electrical pin 520 in the controller connector 120, electrical pin 522 in the wand connector 114, and ultimately to the active electrode 202 (FIG. 3). Likewise, the voltage generator defines a return terminal 524 which couples to electrical pin 526 in the controller connector 120, electrical pin 528 in the wand connector 114, and ultimately to the return electrode 204 (also FIG. 3). Additional active terminals and/or return terminals may be used. The active terminal 518 is the terminal upon which the voltages and electrical currents are induced by the voltage generator 516, and the return terminal 524 provides a return path for electrical currents. It would be possible for the return terminal 524 to provide a common or ground being the same as the common or ground within the balance of the controller 104 (e.g., the common 530 used on push-buttons 132), but in other embodiments the voltage generator 516 may be electrically "floated" from the balance of the controller 104, and thus the return terminal 524, when measured with respect to the common or earth ground (e.g., common 530) may show a voltage; however, an electrically floated voltage generator 516 and thus the potential for voltage readings on the return terminals 524 relative to earth ground does not negate the return terminal status of the terminal 524 relative to the active terminal 518.

The AC voltage signal generated and applied between the active terminal 518 and return terminal 524 by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is greater at 100 kHz.

The RMS (root mean square) voltage generated by the voltage generator 516 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 516 for ablation in some embodiments is a square waveform with a peak-to-peak voltage in the range of 10 V to 2000 V, in some cases in the range of 100 V to 1800 V, in other cases in the range of about 28 V to 1200 V, and often in the range of about 100 V to 320V.

The voltage and current generated by the voltage generator 516 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of a square wave voltage produced by the voltage generator 516 is on the order of about 50% for some embodiments as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 516 delivers average energy levels ranging from several milliwatts to hundreds of watts per electrode, depending on the mode of ablation and state of the plasma proximate to the active electrode. In example systems, the voltage generator 516 in combination with the processor 500 are configured to initially set the energy output of the voltage generator 516 (e.g., by controlling output voltage) based on the mode of ablation selected by the surgeon, and in some cases the setpoint within the particular mode of ablation. Moreover, while in a selected mode of ablation and setpoint within the mode of ablation, the processor 500 and/or voltage generator 516 may make control changes to compensate for changes caused by use of the wand. A description of various voltage generators 516 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, entitled "METHOD AND SYSTEM OF AN ELECTROSURGICAL CONTROLLER WITH WAVE-SHAPING", the complete disclosure of which is incorporated herein by reference as if reproduced in full below.

In example systems the voltage generator 516 (along with the peristaltic pump 118) may be controlled by the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output converter 508, or by way of packet-based communications using the communication device 512 (the communication-based embodiments not specifically shown so as not to unduly complicate FIG. 5).

Before proceeding, it is noted that the various embodiments of detecting the state of the useful life of the active electrode, and/or clog detection, may be implemented on systems having a single mode of ablation. Stated otherwise, determining the useful life of the active electrode and/or presence of a clog is not limited to systems having multiple modes of ablation.

During use of the controller 104, the electrode circuit (including the plasma created and maintained in operational relationship to the active electrode of a wand, the fluid between the active and return electrode, and the electrode-fluid interface) has or presents a certain amount of impedance to the flow of energy from the active electrode toward a return electrode. The impedance presented by the electrode circuit may be dependent on many factors, including but not limited to the thickness and volume of the plasma itself, the surface area of the active electrode, the surface area of the active electrode not covered by a vapor layer and directly in contact with the conductive fluid, and the volume flow of fluid and/or gasses away from the location of the plasma. In example systems, voltage generator 516 is a "constant voltage source", meaning that the voltage generator 516 provides the voltage requested by the processor 500 (at the frequency and duty cycle) largely independent of the impedance presented by the electrode circuit. In such systems, the controller 104 may comprise a mechanism to sense the electrical current provided to the active electrode. In the illustrative case of FIG. 3, sensing electrical current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the digital-to-analog converter 514 (as shown by 16 the bubble A). In some cases, the current sense transformer may couple directly to the analog-to-digital converter 514, and in other cases additional circuitry may be imposed between the current sense transformer 532 and the digital-to-analog converter 514, such as amplification circuits and protection circuits. For example, in one example system the current sense transformer 532 is coupled to an integrated circuit device that takes the indication of current from the current sense transformer 532, calculates a RMS current value, and provides the RMS current values to the processor 500 through any suitable communication system (e.g., as an analog value applied the A/D 514, as a digital value applied to the multiple inputs of the D/I 510, as a packet message through the communication port 512).

The current sense transformer is merely illustrative of any suitable mechanism to sense the electrical current supplied to the active electrode, and other systems are possible. For example, a small resistor (e.g., 1 Ohm, 0.1 Ohm) may be placed in series with the active terminal 518, and the voltage drop induced across the resistor used as an indication of the electrical current.

Given that the voltage generator 516 is electrically floated, the mechanism to sense current is not limited to the just the active terminal 518. Thus, in yet still further embodiments, the mechanism to sense current may be implemented with respect to the return terminal 524. For example, illustrative current sense transformer 532 may be implemented on a conductor associated with the return terminal 524.

While the example voltage generator of FIG. 4 is a "constant voltage source", and thus electrical current may change based on the impedance presented by the electrode circuit, other types of generators may be implemented in connection with determining useful life of the active electrode and/or clog detection. For example, the generator may be a "constant current source", in which case the voltage applied to the active terminal may change depending on the impedance. In the "constant current source" situation the electrical current may be known based on the setpoint, and thus the voltage as measured between the active terminal and the return terminal may change depending on the impedance. Regardless of the type of generator, knowing the "constant" electrical parameter and measuring a changing electrical parameter enables the controller 104 to calculate power supplied to the active electrode 202 of the wand 102. However, power is merely the product of electrical current and applied voltage, and thus for a "constant voltage source" the electrical current alone is directly indicative of power provided. Likewise, for a "constant current source" the applied voltage alone is directly indicative of power provided. It follows that the controller need not necessarily calculate power to monitor electrical energy supplied to the active electrode.

Even in the case of a constant voltage source, the controller 104 may nevertheless measure voltage. Thus, in some cases the active terminal 518 may be electrically coupled to the digital-to-analog converter 514 (as shown by bubble B). However, additional circuitry may be imposed between the active terminal 518 and the digital-to-analog converter 514, for example various step-down transformers, protection circuits, and circuits to account for the electrically floated nature of the voltage generator 516. Such additional circuitry is not shown so as not to unduly complicate the figure. In yet still other cases, voltage sense circuitry may measure the voltage, and the measured voltage values may be provided other than by analog signal, such as by way of packet-based communications over the communication port 512 (not shown so as not to unduly complicate the drawing).

Still referring to FIG. 5 (and also FIG. 1), controller 104 in accordance with example systems further comprises peristaltic pump 118. The peristaltic pump comprises rotor 124 mechanically coupled to a shaft of the electric motor 534. In some cases, and as illustrated, the rotor of the electric motor may couple directly to the rotor 124, but in other cases various gears, pulleys, and/or belts may reside between the electric motor 534 and the rotor 124. The electric motor 534 may take any suitable form, such as an AC motor, a DC motor, and/or a stepper-motor. To control speed of the shaft of the electric motor 534, and thus to control speed of the rotor 124 (and the volume flow rate at the wand), the electric motor 534 may be coupled to a motor speed control circuit 536. In the illustrative case of an AC motor, the motor speed control circuit 536 may control the voltage and frequency applied to the electric motor 534. In the case of a DC motor, the motor speed control circuit 536 may control the DC voltage applied to the electric motor 534. In the case of a stepper-motor, the motor speed control circuit 536 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn.

The processor 500 couples to the motor speed control circuit 536, such as by way of the digital-to-analog converter 506 (as shown by bubble C). The processor 500 may be coupled in other ways as well, such as packet-based communication over the communication port 512. Thus, the processor 500, running a program, may read electrical current supplied on the active terminal 518, may read voltage supplied on the active terminal 518, and responsive thereto may make speed control changes (and thus volume flow rate changes) by sending speed commands to the motor speed control circuit 536. The motor speed control circuit 536, in turn, implements the speed control changes. Speed control changes may comprise changes in speed of the rotor 124 when desired, stopping the rotor 124 when desired, and in some modes of ablation temporarily reversing the rotor 124.

State of the Useful Life of the Active Electrode

The specification now turns to example embodiments of detecting when the active electrode of the wand 102 is approaching, has reached, or has exceeded the useful life of the active electrode 202. When a wand 102 is new, the active electrode 202 has a certain size, a certain exposed surface area (e.g., that portion not abutting the spacer 200), and various edges or asperities. However, plasma created proximate the active electrode 202 molecularly dissociates tissue proximate the plasma, and the plasma also removes (i.e., etches) material of the active electrode 202 itself. As the etching takes place, the exposed surface area of the active electrode 202 is reduced, and the sharp edges are smoothed.

After a certain amount of use, while metallic material of the active electrode 202 may still be present on the distal tip of the wand, the size of the plasma created proximate the active electrode 202 may be reduced (because of the smaller exposed surface area) to the point that the therapeutic benefit is no longer achievable, or the reduced therapeutic benefit is outweighed by other factors (e.g., damage caused by extending the time of the procedure, non-ablative contact with tissue within the joint that causes bruising or further injury). Similarly, for an active electrode 202 such as discussed above where the aspiration of the ablated tissue and other fluids is through the active electrode 202 itself, after a certain amount of use the reduction in the metallic material present on the active electrode 202 may increase the size of the aperture 402 through the active electrode 202. Thus, aspiration flow may increase (compared to a "new" wand 102) to the point that the therapeutic benefit is no longer achievable, or the reduced therapeutic benefit is outweighed by other factors. If follows that, in discussing useful life of an active electrode, it is to be understood that the active electrode 202 may still be physically present and perhaps usable, at least in a limited sense, at the point in time that the "useful life" has been met or exceeded.

Even with a new active electrode, during ablative procedures the impedance presented by the electrode circuit may vary significantly. For example, impedance presented during periods of time when the active electrode 202 is close to and is ablating tissue is relatively high. Impedance may be relatively low when the wand is active but in saline with high flow. Different impedance may be presented by the electrode circuit based on different tissue types being ablated. Moreover, during use the plasma periodically is extinguished and re-ignited, causing impedance changes.

As the exposed surface area of the active electrode 202 is reduced, the impedance presented by the electrode circuit is increased. Another characteristic of an active electrode when exposed surface area is reduced is that creation and forming the vapor layer around the active electrode 202 is easier and thus creation of and maintaining plasma by the controller 104 is easier. It follows that variation in impedance presented by the electrode circuit is reduced as the exposed surface area of the active electrode is reduced.

In accordance with example embodiments, the controller 104 may make a determination as to the state of the useful life of the active electrode based on an electrical parameter associated with the plasma. More particularly, in example systems the controller 104 may maintain plasma proximate the active electrode 202, and during periods of time when plasma is present the controller 104 monitors the electrical parameter associated with the plasma. For example, in cases where the generator 516 is a constant voltage source generator, the controller may monitor electrical current supplied on the active terminal 518 (e.g., monitor by way of current sense transformer 532). In cases where the generator is a constant current source generator, the controller may monitor voltage supplied across the active terminal 518 and return terminal 524. In some cases the monitored electrical parameter alone is sufficiently related to impedance that an actual value of impedance need not be calculated, but having the controller 104 calculate a value of impedance is also possible. In other cases, power delivered to the electrode circuit (which is also related to impedance) may be calculated.

Regardless of the electrical parameter monitored or calculated, in example systems the controller 104 further determines, based on the electrical parameter, the presence of a wand condition of the electrosurgical wand 102. The wand condition may be that the exposed surface area of the active electrode is less than a predetermined threshold surface area (e.g., the wand has exceeded its useful life), or that the surface area of the active electrode is approaching the predetermined threshold surface area (e.g., the wand is approaching the end of its useful life).

In accordance with example systems, the determination regarding state of the useful life of the active electrode may be based on variation of the electrical parameter over a predetermined period of use. That is, over a predetermined period of use (e.g., the immediately previous 5 to 15 seconds of use), the controller 104 may calculate a value indicative of variation of the monitored electrical parameter (hereafter just "variation metric"), and make the determination based on the variation metric. For example, if the variation metric gets smaller as the variation in impedance presented by the electrode circuit is reduced, then the controller may determine that the wand condition is present when the variation metric falls below a predetermined value. It is also possible to calculate a variation metric that is inversely proportional to variation of the electrical parameter (e.g., increases as the variation in impedance presented by the electrode circuit is reduced), and in such cases the controller may determine that the wand condition is present when the variation metric meets or exceeds a predetermined value.

In some example systems, the variation metric alone is sufficient to determine when the active electrode is approaching, has met, or has exceeded its useful life. However, variations in impedance presented in the electrode circuit during use may mimic a worn electrode when the electrode still has useful life, or may mask the fact that the active electrode is worn. In yet still further example systems then, the determination as to the state of the active electrode may also be based on or confirmed by other measured or monitored parameters.

Referring briefly to FIGS. 3 and 4, in the example system discussed in this specification aspiration of the ablated tissue and other fluids is through an aspiration aperture 402 in the active electrode and a corresponding distal opening 404 in the wand 102. The ablated tissue and other fluids move through the suction lumen 300 and then through the tubular member 116 past the temperature measurement device 304. Controller 104 may thus read the temperature (or a value indicative of temperature) of the aspirated fluids by way of the temperature measurement device 304. When a wand 102 is new and the active electrode has its largest exposed surface area, the amount of energy that can be applied to the plasma and surrounding tissue is high, but as the exposed surface area is reduced the amount of energy that can be applied is reduced. It follows that the temperature of the fluids drawn into the suction lumen 300 and through the tubular member 116 is reduced as the exposed surface area of the active electrode is reduced.

In further example systems, the determination as to whether the active electrode is approaching, has reached, or has exceeded its useful life may be further based on the temperature measured by the temperature measurement device 304 during the predetermined period of use. In particular, during the predetermined period of use (e.g., the immediately previous 5 to 15 seconds of use) the controller 104 calculates the variation metric, reads the temperature of the aspirated fluids, and makes the determination as to the state of the useful life of the active electrode based on the variation metric and the temperature. For example, the controller 104 may determine that the wand condition is present when the variation metric falls below a predetermined value and one of the following temperature conditions is present: the temperature is below a predetermined threshold temperature; the temperature is above the predetermined threshold temperature but trending toward the predetermined threshold temperature; the temperature is trending downward (regardless of initial temperature); or the rate of change of the temperature (i.e., the slope) meets or exceeds a predetermined rate.

If the temperature is below the predetermined threshold temperature, such may indicate that the exposed surface area of the active electrode has been reduced and therefore the amount of energy that can be applied by the controller 104 (and the temperature of the surrounding fluid) is similarly reduced. Thus, the temperature being below the predetermined threshold temperature may be indicative of the active electrode having exceeded its useful life. As for the second temperature condition, on the same physical considerations as the first temperature condition, the temperature being above the predetermined threshold temperature is initially indicative of an active electrode with remaining useful life, but trending of the temperature downward toward the threshold temperature may indicate that the active electrode is approaching the end of its useful life. In yet still other cases, the trend of temperature may be used with a need to evaluate an initial temperature. For example, for a certain energy input, if the slope is negative, such a negative slope may be indicative of a worn active electrode. The specification now turns to consideration of selecting the predetermined periods of use, predetermined values regarding the variation metric, predetermined threshold temperatures, and/or predetermined slopes regarding temperatures.

The various predetermined periods, values, and temperatures may be different for different wands, different uses of the wands, different energy levels provided by controllers, different joint and/or room temperatures, and different aspiration rates, to name a few. Moreover, some electrosurgical systems, like those discussed in this specification, have the ability to operate in varying modes of ablation, and thus a single controller 104 and a single wand 102 may be operated in several different energy ranges and aspiration rates even within the same surgical procedure. For example, the controller of this specification may implement: a "low mode" which may be used for treatment, ablation, and removal of portions of cartilage; a "medium mode" which may be used for treatment, ablation, and removal of meniscus; a "high mode" which may be used for aggressive treatment, ablation, and removal of tissue; and a "vacuum mode" for removal of loose, free floating and/or trapped tissue. Each illustrative mode of ablation may be characterized by a range of energies that may be applied to the active electrode (hereafter just "energy range") and a corresponding range of aspiration flows.

The various predetermined periods, values, and temperatures will be different for different for different modes of ablation. That is, the predetermined value of the variation metric that may indicate a worn electrode in the low mode may be lower than the predetermined value of the variation metric that may indicate a worn electrode in the high mode. Similarly, the predetermined threshold temperature that may indicate a worn electrode in the low mode may be lower than the predetermined threshold temperature that may indicate a worn electrode in the high mode. Further still, because the variation may be smaller in the example low mode, the predetermined period of use in the low may be longer than the predetermined period of use in the high mode. It will be further understood that within the same electrosurgical procedure, as the surgeon switches between modes of ablation but using the same wand, the various predetermined periods, values, and temperatures may likewise change. A wand may have a longer useful life if operated exclusively in the low mode of ablation, but the useful life may get shorter with increasing use times in the higher modes of ablation.

Determining the various predetermined periods, values, and temperatures may be based on laboratory studies that characterize the wands in different uses, energy ranges, and aspiration flow rates. Moreover, electrosurgical controllers may have the ability to store data associated with an electrosurgical procedure, and based on offline analysis engineers may quantify when an active electrode met or exceeded its useful life, and then set values for future use accordingly.

In some systems, the various predetermined periods, values, and temperatures are stored in a non-volatile memory of the controller 104 (e.g., the ROM 502). Once the controller 104 identifies the wand (either automatically, or by the user inputting the information using buttons 132 and/or display device 130), the appropriate predetermined periods, values, and temperatures are read and applied during use. In other systems, the various predetermined periods, values, and temperatures are stored on the wand 102. For example, and referring briefly to FIG. 3, the non-volatile memory 308 associated with the processor 306 may store the various predetermined periods, values, and temperatures (for a single mode of ablation, or for multiple modes of ablation). The controller 104 may read data from the processor 306 (such as over 310), and then apply the data during the electrosurgical procedure.

Blockage Detection

In researching and developing the various algorithms to determine when an active electrode has met or exceeded its useful life, the inventors of the present specification found that the various methods regarding determining useful life of the active electrode may also be used to detect clogging of the wand (such as by large pieces of tissue blocking aspiration flow) In particular, when fluid flow through a wand is either fully or at least partially blocked, either at the active electrode or within the suction tubing, the aspiration flow is reduced or stops completely. The reduced or lack of aspiration flow tends to stabilize the plasma, resulting in a lower variation of impedance presented by the electrode circuit. Further, because the reduced flow of fluids, the temperature measured by the temperature measurement device 304 starts to fall. For example, if the temperature measurement device 304 is a RTD, the RTD has a certain thermal mass which will retain the last temperature measured, and then show lowering temperatures as the thermal mass of the RTD cools.

Thus, the clog situation presents itself similarly to the worn electrode—low variation in impedance and slowly descending temperatures. In some cases, the controller may not be able to distinguish between a worn electrode and a clog, and may thus classify the event as a wand condition that could be either situation.

Flow Diagram

Figure 6A:
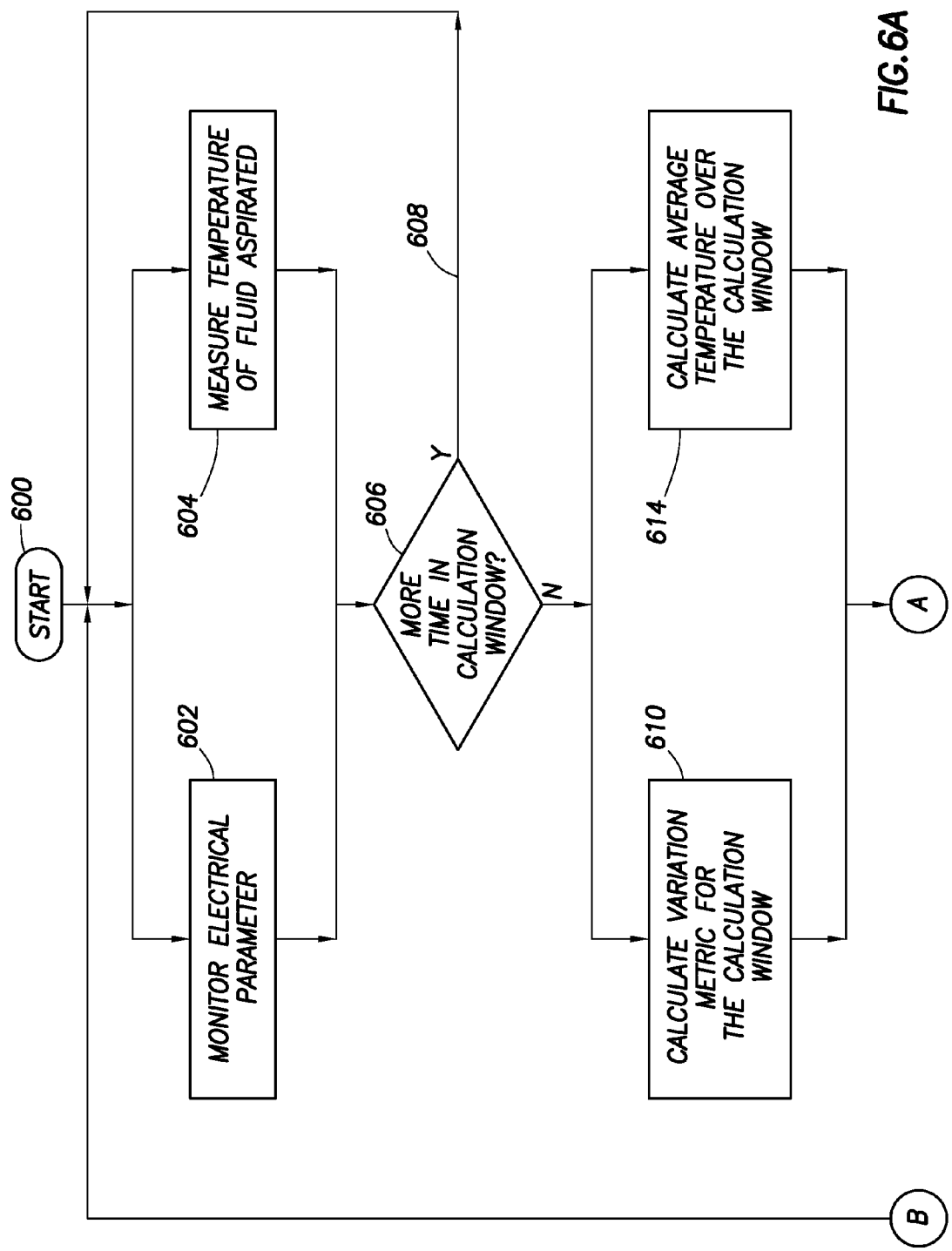
FIG. 6 (comprising FIGS. 6A and 6B) shows a flow diagram in accordance with at least some embodiments.
Figure 6B:
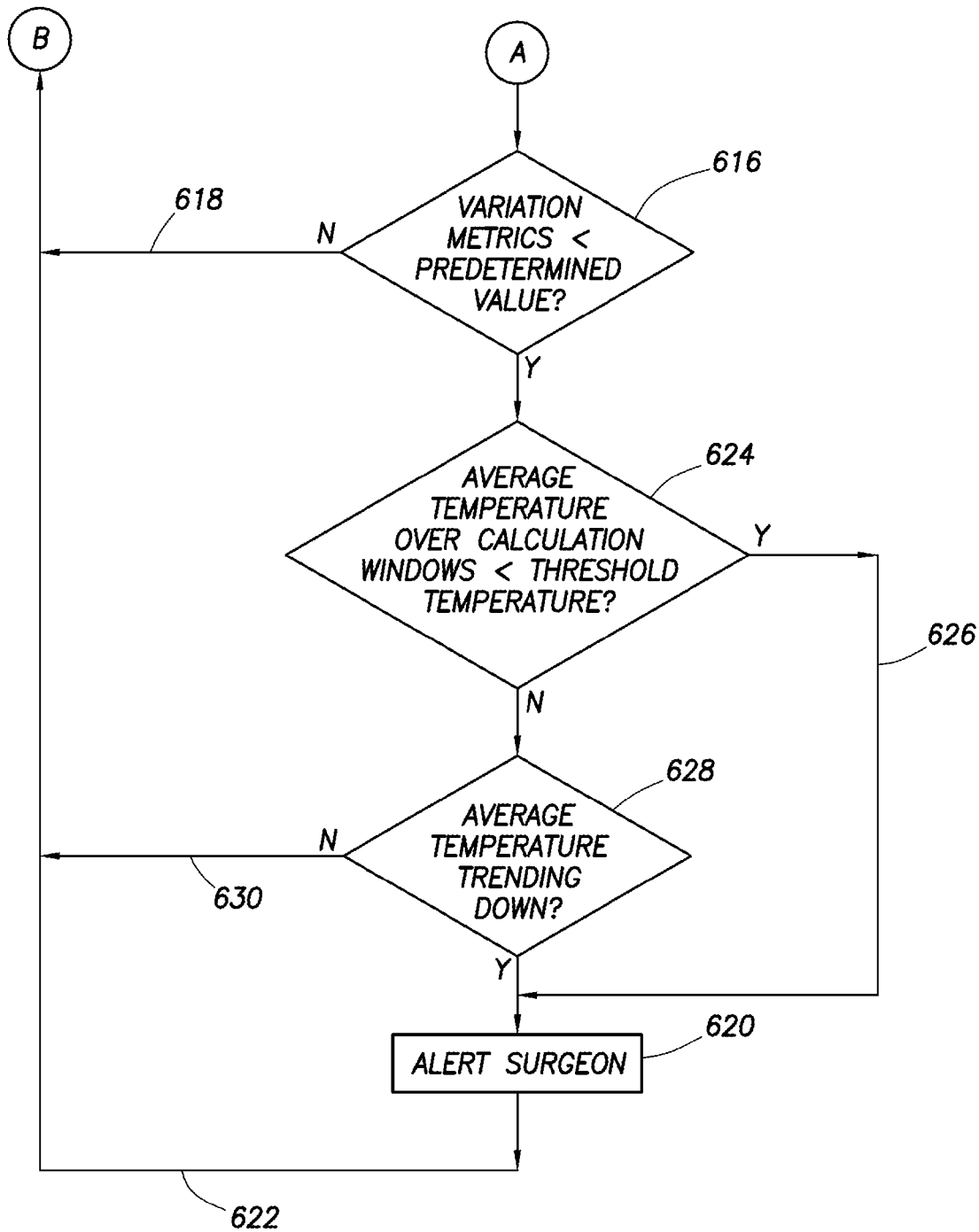

The specification now turns to a description of an example implementation in greater detail. FIG. 6 (comprising FIGS. 6A and 6B) shows a flow diagram of a method which may be implemented on the processor 500 of the controller 104. So as not to unduly complicate the figure and the description, FIG. 6 is based on several underlying assumptions. First, the flow diagram of FIG. 6 assumes that the generator 516 of the controller 104 is applying energy to the active electrode 202 of the wand 102 and that the voltage applied is high enough to produce plasma on the active electrode. If the surgeon stops the application of energy, the example method implemented by the flow diagram pauses until such time that the energy is restarted. Second, the flow diagram of FIG. 6 assumes that the energy has been active over a previous predetermined period of use (and the use over predetermined period of use may be fulfilled by tacking together periods of time when the energy is being applied even if separated by periods when the energy has been turned off). One having ordinary skill in the art, after understanding the example method, could easily modify the programming to account for initial use leading up to use over a complete predetermined period of use, and taking into account periods of time when the energy is turned off. Third, the various predetermined periods, values, and temperatures have already been read by or provided to the controller 104, including the various predetermined periods, values, and temperatures for each mode of ablation if the controller implements multiple modes of ablation. Fourth, the variation metric is directly proportional to variance of the electrical parameter. One having ordinary skill in the art, after understanding the example method, could easily modify the programming to account for a variation metric that is inversely proportional to variation of the electrical parameter.

With the assumptions in mind, the method starts (block 600) and proceeds to monitoring an electrical parameter associated with the applied energy (block 602). The monitoring could be measuring electrical current supplied to the active electrode, measuring voltage applied across the active and return electrodes, or calculating further parameters based on the electrical current or voltage (e.g., impedance, instantaneous power). In cases where temperature is a component the overall determinations, simultaneously with monitoring the electrical parameter, the method may further include reading or measuring temperature of fluid aspirated (block 604) (e.g., reading or measuring a value indicative of temperature associated with the fluid drawn in the vicinity of the active electrode).

The illustrative method then proceeds to making a determination as to whether more time remains in the current calculation window (block 606). In particular, the predetermined period of use (e.g., the immediately previous 5 to 15 seconds of use) is conceptually divided into a plurality of calculation windows of time (e.g., four to eight calculation windows). In one example implementation, each calculation may be one second in duration, and thus for a predetermined period of use of five seconds, five calculation windows may be used. In another example implementation, two second calculation windows may be used, and thus for a predetermined period of use of 14 seconds, seven calculation windows may be used. Thus, if there is more time needed to complete a calculation window (again block 606), the illustrative method returns (along path 608) to again monitor the electrical parameter (block 602) and measuring the temperature (block 604).

If the time duration of the current calculation window has been met (again block 606), the example method then proceeds to calculating a variation metric over the just-concluded calculation window (block 610). The variation metric can be conceptually thought of as the mathematical variance of the measured electrical parameter measurements; however, the controller 104 need not necessarily calculate an actual variance value. For example, in order to reduce processing overhead, the variation metric may be calculated by subtracting measured values between consecutive measurements to obtain difference values, and then summing the absolute values of the differences values. Other methods to calculate the variation metric may also be implemented in example embodiments, included calculating actual variance if sufficient processor cycles are available.

Still referring to FIG. 6A, again in cases where temperature is a component the overall determinations, simultaneously with calculating the variation metric (block 610), the method may further include calculating an average temperature over the current calculation window (block 614) assuming many temperature measurements are made in the calculation window. The method contemplates calculation windows having only a single reading or measurement of a value indicative of temperature, in which case the calculating the average is mooted. In order to reduce processor cycles a value proportional to average may be calculated instead of an actual average.

The example method may then proceed to a determination as to whether the variation metrics are less all than a predetermined value for each of the calculation windows (block 616). If the variation metrics are all above the predetermined value, the active electrode may still have sufficient useful life, and thus the example method retreats to the beginning (along path 618) to begin anew in the next calculation window. On the other hand, if the variation metrics are all below the predetermined value, such may indicative that the active electrode 202 of the wand 102 is approaching, has reached, or has exceeded its useful life, or fluid flow through the wand is either fully or at least partially blocked. In some example systems the determination regarding the variation metric alone may be sufficient, and thus the system may alert the surgeon (block 620) and the example method moves again to the beginning (along path 622) to begin anew in the next calculation window.

However, in other cases the determination regarding useful life of the active electrode may be augmented by a temperature component. Thus, if the variation metric are below the predetermined threshold (again block 616), the example method proceeds to temperature aspects of the overall determination. In the first temperature aspect, a determination is made as to whether the average temperature for each calculation window of the predetermined measurement period is below a predetermined threshold temperature (block 624). If so, the example method proceeds along path 626 to alerting the surgeon (again block 620). On the other hand, if the average temperature for each calculation window of the predetermined measurement period is above the predetermined threshold temperature (again block 624), the example method moves to a determination as to whether average temperature of each calculation window, when considered as a group, is trending toward the predetermined threshold temperature (block 628). If not, the example method retreats to the beginning (along path 630) to begin anew in the next calculation window. If so, the method proceeds to alerting the surgeon (again block 620).

The above discussion is meant to be illustrative of the principles and various embodiments of the present invention. Numerous variations and modifications are possible. As an example, while useful life and/or clog detection has been described as taking place within an electrosurgical controller, the determinations regarding useful life and/or clog detection could also be made in a standalone system operationally coupled to an electrosurgical controller and monitoring the various parameters. For example, the standalone system could be imposed between the electrosurgical controller and the wand and passively obtain the various parameters used to make the useful life and/or clog detection. In other cases, the standalone system may communicatively couple to the electrosurgical controller and receive data regarding the ablation procedure, and make the various determinations. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method comprising:
    supplying energy to an active electrode of an electrosurgical wand by an electrosurgical controller;
    monitoring an electrical parameter associated with the energy; and
    determining, based on the electrical parameter, presence of a wand condition of the electrosurgical wand, the wand condition being at least one selected from the group consisting of: a surface area of the active electrode is less than a predetermined threshold surface area; and the surface area of the active electrode is approaching the predetermined threshold surface area.

2. The method of claim 1 wherein determining further comprises:
    calculating a value indicative of variation of the electrical parameter over at least a portion of the predetermined period of use; and
    determining the presence of the wand condition based on the value indicative of variation of the electrical parameter.

3. The method of claim 2 wherein determining the presence of the wand condition based on the value indicative of variation of the electrical parameter further comprises determining the wand condition as present when the value indicative of variation of the electrical parameter is below a predetermined value.

4. The method of claim 2:
    wherein calculating the value indicative of variation of the electrical parameter further comprises:
        calculating a value indicative of variation of the electrical parameter for each of a plurality of calculation windows, the plurality of calculation windows residing within the predetermined period of use;
    wherein determining the presence of the wand condition further comprises determining the wand condition to be present when the values indicative of variation of the electrical parameter are below a predetermined value.

5. The method of claim 1 wherein monitoring the electrical parameter further comprises monitoring at least one parameter selected from the group consisting of: impedance; voltage applied; electrical current applied; and power provided.

6. The method of claim 1 further comprising:
    measuring a value indicative of temperature of a fluid drawn from a vicinity of the active electrode, the measuring over a predetermined period of use;
    wherein determining the presence of the wand condition further comprising determining based on the electrical parameter and the value indicative of temperature.

7. The method of claim 6 wherein measuring the value indicative of temperature further comprises measuring a temperature of fluid within a suction lumen of the electrosurgical wand.

8. The method of claim 6 wherein measuring the value indicative of temperature further comprises measuring a temperature of tubing through which the fluid is drawn.

9. The method of claim 8 wherein measuring a temperature of the tubing further comprises measuring a temperature of tubing disposed within a handle of the electrosurgical wand.

10. The method of claim 1 comprising:
    calculating a value indicative of variation of the electrical parameter over a predetermined period of use; and
    measuring a value indicative of temperature associated with fluid drawn from a vicinity of the active electrode, the measuring over the predetermined period of use;
    wherein determining the presence of the wand condition further comprises determining based on the value indicative of variation of the electrical parameter the value indicative of temperature.

11. The method of claim 10 wherein determining the presence of the wand condition further comprises determining wand condition as present when the value indicative of variation of the electrical parameter is below a predetermined value and the value indicative of temperature is at least one selected from the group consisting of: below a predetermined threshold temperature; above the predetermined threshold temperature with a temperature trending toward the predetermined threshold temperature; trending downward; has or exceeds a predetermined rate of change.

12. The method of claim 10 further comprising:
    wherein calculating the value indicative of variation of the electrical parameter further comprises calculating a value indicative of variation of the electrical parameter for each of a plurality of calculation windows, the plurality of calculation windows residing within the predetermined period of use; and
    wherein measuring the value indicative of temperature associated with the fluid drawn from the vicinity of the active electrode further comprises measuring a value indicative of temperature for each of the plurality of calculation windows;
    wherein determining the presence of the wand condition further comprises determining the wand condition as present when the value indicative of variation of the electrical parameter is below a predetermined value and the value indicative of temperature for each of the plurality of calculation windows is at least one selected from the group consisting of: below a predetermined threshold temperature; above the predetermined threshold temperature with a temperature trending toward the predetermined threshold temperature; trending downward; has or exceeds a predetermined rate of change.

13. The method of claim 12 wherein monitoring the electrical parameter further comprises monitoring at least one parameter selected from the group consisting of: impedance; voltage applied; electrical current applied; and power supplied.

14. The method of claim 1 further comprising calculating a value indicative of variation of the electrical parameter over at least a portion of a predetermined period of use; and determining that a fluid flow through the electrosurgical wand is at least partially blocked based on the value indicative of variation of the electrical parameter.

15. A method comprising:
supplying energy to an active electrode of an electrosurgical wand by an electrosurgical controller;
monitoring an electrical parameter associated with the energy;
calculating a value indicative of variation of the electrical parameter over at least a portion of a predetermined period of use; and
determining, based on the value indicative of variation of the electrical parameter, presence of a wand condition of the electrosurgical wand, the wand condition being at least one selected from the group consisting of: a surface area of the active electrode is less than a predetermined threshold surface area; and the surface area of the active electrode is approaching the predetermined threshold surface area; and that a fluid flow through the electrosurgical wand is at least partially blocked.

16. A method comprising:
supplying energy to an active electrode of an electrosurgical wand by an electrosurgical controller;
monitoring an electrical parameter associated with the energy;
measuring a value indicative of temperature of a fluid drawn from a vicinity of the active electrode, the measuring over a predetermined period of use and
determining, based on the electrical parameter and the value indicative of temperature, presence of a wand condition of the electrosurgical wand, the wand condition being at least one selected from the group consisting of: a surface area of the active electrode is less than a predetermined threshold surface area; and the surface area of the active electrode is approaching the predetermined threshold surface.

\* \* \* \* \*